(12) United States Patent
Zech et al.

(10) Patent No.: US 6,894,144 B1
(45) Date of Patent: May 17, 2005

(54) TWO-CONSTITUENT ELASTOMER MATERIALS BASED ON ALKYL AZIRIDINE COMPRISING A CATALYST CONSTITUENT THAT CONTAINS A BORIC ACID COMPLEX

(75) Inventors: Joachim Zech, Kaufering (DE); Gunther Eckhardt, Bad Duerrenberg (DE); Cornelia Führer, Wertach (DE); Bernd Gangnus, Andechs (DE); Andreas Rombach, Herrsching (DE); Oswald Gasser, Seefeld (DE); Thomas Klettke, Schondorf (DE); Erich Wanek, Kaufering (DE)

(73) Assignee: 3M Espe AG, Seefeld (DE)

( * ) Notice: Subject to any disclaimer, the term of this patent is extended or adjusted under 35 U.S.C. 154(b) by 240 days.

(21) Appl. No.: 10/070,376

(22) PCT Filed: Sep. 1, 2000

(86) PCT No.: PCT/EP00/08568

§ 371 (c)(1),
(2), (4) Date: May 6, 2002

(87) PCT Pub. No.: WO01/17483

PCT Pub. Date: Mar. 15, 2001

(30) Foreign Application Priority Data

Sep. 6, 1999 (DE) .......................................... 199 42 459

(51) Int. Cl.⁷ .............................................. C08G 79/38
(52) U.S. Cl. .......................... 528/394; 528/91; 528/486; 156/35; 267/16; 267/222

(58) Field of Search .......................... 528/394, 91, 486; 156/35; 164/16, 222

(56) References Cited

FOREIGN PATENT DOCUMENTS

| DE | 37 28 216 | 3/1988 |
|----|-----------|--------|
| DE | 197 53 461 | 6/1999 |
| EP | 0 279 238 A1 | 8/1988 |
| EP | 0 421 371 A2 | 4/1991 |

*Primary Examiner*—Duc Truong
(74) *Attorney, Agent, or Firm*—Birch, Stewart, Kolasch & Birch, LLP

(57) ABSTRACT

The invention relates to elastomer materials based on N-alkylaziridino compounds with a base component which contains the aziridino compounds and with a catalyst component which contains at least one acid-acting compound, both components being mixed before use, characterized in that, as acid-acting compound of the catalyst component, one or more boric acid complexes are used which can be obtained by reaction of boric acid and/or a boric acid derivative with at least one OH-functional compound, the OH functions being able to be present wholly or partly protected, and this reaction being carried out either as an upstream reaction between boric acid and/or a boric acid derivative and at least one such OH-functional compound or during or after the preparation of the catalyst component or by mixing the catalyst component with the base component which then contains at least one OH-functional compound. The elastomer materials are preferably used as dental impression materials, bite-registration materials and doubling materials.

27 Claims, No Drawings

TWO-CONSTITUENT ELASTOMER MATERIALS BASED ON ALKYL AZIRIDINE COMPRISING A CATALYST CONSTITUENT THAT CONTAINS A BORIC ACID COMPLEX

This application is the national phase under 35 U.S.C. § 371 of PCT International Application No. PCT/EP00/08568 which has an International filing date of Sep. 1, 2000, which designated the United States of America.

The invention relates to improved elastomer materials based on N-alkylaziridino compounds.

In particular, the invention relates to elastomer materials which are characterized by an increased extensibility and are preferably used as dental impression materials, bite-registration materials and doubling materials.

The preparation of elastomer materials based on N-alkylaziridino polyethers and their use in dental materials has been known for a long time. Thus, for example, DE-C-1 745 810 describes the preparation of shaped bodies based on aziridino polyethers.

In the documents DE-C-3 246 654, EP-A-0 421 371 and EP-A-0 110 429, the use of aziridino polyethers in polyether impression materials is described.

It is furthermore known that N-alkylaziridino compounds can cure when exposed to the action of acid-acting compounds (H. Bestian, Methoden der Organischen Chemie [Methods in Organic Chemistry] (Houben-Weyl), XII/1 (1958)). The use of neutral sulphuric acid or sulphonic acid esters as starter substances for the curing of N-alkylaziridino compounds is described in DE-C-888 170.

The use of oxonium, ammonium and sulphonium salts as starter substances is proposed in DE-C-914 325.

A summary of the starter substances used for the curing of aziridino compounds is contained in O. C. DERMER, G. E. HAM, "Ethylenimine and other Aziridines" Academic Press (1969).

Accordingly, a large number of compound classes and compounds have proved to be suitable polymerization initiators in principle. In the practical curing of aziridino polyethers, however, it is very difficult to set the desired setting pattern with a sufficiently long processing time and rapid final curing. This object can be achieved by the use of special trisalkylsulphonium salts according to EP-A-0 279 238.

A disadvantage when using sulphonium salts as starter substances is the compounds which form during curing, which have an unpleasant smell.

If strong acids are improperly used as starter substances, there can be an irritant effect on the skin, or corrosion phenomena can occur on metals.

For use, the mechanical properties such as breaking strength and elongation at break of the cured dental materials are of great importance. These properties are in general at a low level when using the known starter substances.

The object of the invention is to provided curable preparations containing N-alkylaziridino compounds, during the use of which no unpleasantly smelling compounds form, the use of strong, corrosive acids being avoided and the cured dental materials having improved mechanical properties.

This object is achieved by an improved elastomer material based on N-alkylaziridino compounds, with a base component which contains the aziridino compounds, and with a catalyst component which contains at least one acid-acting compound, both components being mixed before use, characterized in that, as an acid-acting compound of the catalyst component, one or more boric acid complexes are used, which can be obtained by reaction of boric acid and/or a boric acid derivative with at least one OH-functional compound, the OH functions being able to be wholly or partly protected, and this reaction taking place either as an upstream reaction between boric acid and/or a boric acid derivative and at least one such OH-functional compound or during or after the preparation of the catalyst component or by mixing the catalyst component with the base component which then contains one such OH-functional compound.

The elastomer material preferably consists only of the base component and the catalyst component.

The improved elastomer materials according to the invention are used for example as dental impression materials, as bite-registration materials and as doubling materials.

The cured materials surprisingly also display markedly improved mechanical properties. Clearly, the mechanical properties, such as breaking strength and elongation at break of the cured materials, can be influenced through the selection of starter substances.

The boric acid or the boric acid derivatives used as a constituent of the catalyst component are used in a proportion by mass of 0.1 to 100% of the catalyst compound.

Favourable results with regard to the improvement of the mechanical properties can be achieved if the ratio of the number of mols of boric acid to the number of aziridino equivalents in the cured materials is 1:1 to 1:20, preferably 1:1.2 to 1:10 and particularly preferably 1:1.5 to 1:6, the aziridino equivalent mass of the N-alkylaziridino compounds used lying in the range from 500 to 25000 g/equivalent, preferably in the range from 1000 to 8000 g/equivalent and particularly preferably in the range from 2000 to 6000 g/equivalent.

It has long been known that polyol compounds such as sugar, sugar alcohols, sugar acids and uronic acids form ester-like complexes with boric acid. A summary of the analytically relevant results is contained in "Treatise on Analytical Chemistry", Part II, Vol. 10, Wiley, New York.

This complex formation is associated with an increase in acidity and allows the easily-realized alkalimetric titration of boric acid.

Complex formation is however also used in chromatographic and conductimetric analysis processes and in processes for the industrial extraction of boric acid from aqueous mixtures containing same.

Well-examined complexing agents for boric acid with regard to alkalimetric titration are fructose, glycose, mannitol, sorbitol and glycerol; the ionisation constants and the stability constants of the respective complexes are given (W. A. Nasarenko et al., Zaw. Lab. 34 (1968), 257).

Surprisingly it was found that boric acid complexes with OH-functionalized compounds are in a position to effect the curing of N-alkylaziridino compounds at room temperature and at a useful speed, which is mostly not the case with Brönsted acids which possess approximately the same $pK_s$ value as these complexes.

The discovery that, by using selected polyol boric acid complexes, the level of the mechanical properties can be clearly improved was also wholly surprising.

It was furthermore found that both during the formation of the complexes and during the curing of the N-Alkylaziridino polyethers, no unpleasantly smelling compounds form.

Furthermore, the irritant effect of the catalyst component on the skin, for example when not properly used, and also the corrosive effect on base metals can be markedly reduced or avoided through the choice of complexing agents.

The reaction products of boric acid with OH-containing compounds, called "polyol boric acid complexes" in simple terms, to be used in the course of the invention are prepared by reaction of boric acid or boric acid derivatives with compounds which preferably contain at least two OH groups, compounds with only one OH group also being able to be used in the complexing.

According to the invention, OH-functional compounds are used which contain at least one and up to 10 OH groups of the general structural formula

R1, R2 and R3 representing the same or different radicals which are hydrogen, aliphatic, cycloaliphatic, aromatic or araliphatic substituents with 1 to 30 C atoms in each of which one or more C atoms can be replaced by

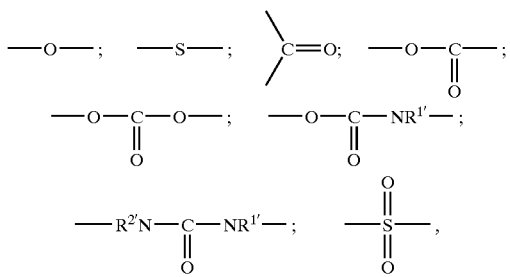

R1 and R2 being the same or different and aliphatic, cycloaliphatic, aromatic or araliphatic bivalent radicals with 1 to 30 C atoms.

In the complexing agents with two OH groups used according to a preferred version of the invention, these can be present in 1,2 position, in 1,3 position or in a different position if the conformation of these compounds allows the formation of relatively stable complexes. The 1,2 position and the 1,3 position are preferred.

When using alcohols with more than two OH groups, different positions of these OH groups are possible. The 1,2,3 position such as is present in some sugars is favourable.

Complexing agents which have at least one phenolic OH group are used to advantage. In this case, compounds are particularly preferred which also carry at least one other phenolic OH group or an aliphatic OH group and optionally further substituents at the aromatic core.

Another preferred group of the complexing agents additionally or exclusively contains carboxylic OH groups. Particularly preferred in this case are compounds which carry an aliphatic OH group in alpha position relative to the carboxyl group.

Typical representatives of the complexing agents for the use according to the invention are:
1. Glycerol and its ether or ester derivatives as well as alkoxy-extended glycerols and polyglycerols, such as for example diglycerol, tetraglycerol, glycerol propoxylate,
2. Alkylene glycols such as ethylene glycol and propylene glycol and polyalkylene glycols such as for example polyethylene glycol, polypropylene glycol, polyethylene glycol monomethyl ether,
3. Mono- and multi-1,2-diols with alkyl radicals or alkylene bridges such as for example 1,2-hexanediol, 1,2-cyclohexanediol, 3-chloropropan-1,2-diol, 1,2-propanediol, 3-mercapto-1,2-propanediol, pinacol, 3-bromopropan-1,2-diol, 1,2-butanediol and 1,2,9,10-tetrahydrodecane,
4. Mono- and multi-1,3-diols with alkyl radicals or alkylene bridges such as 1,3-butanediol, 2-ethyl-1,3-hexanediol, 2-ethyl-2-butylpropan-1,3-diol, 1,3-butanediol, 1,3-cyclohexanediol, 1,3-hexanediol, 2,2-diethylpropan-1,3-diol, 2,4-pentanediol, 2-methyl-2-propyl-1,3-propanediol, 2,2-dimethylpropan-1,3-diol, as well as diols such as 1,5-butanediol, 1,6-hexanediol, cis-2-buten-1,4-diol, 2-butin-1,4-diol, and alpha, omega-OH-functionalized polymers such as poly-THF,
5. Polyalcohols such as glucose, fructose, lactose, arabinose, ribose, xylose, mannose, galactose, sorbose, xylulose, ribulose, mannitol, sorbitol, maltitol, lactitol, gluconitrilol, pentaerythritol, threitol, erythritol, arabitol,
6. Hydroxycarboxylic acids such as gluconic acid, 2-ketogluconic acid, mannosaccharic acid, mucic acid, glucuronic acid, quinic acid, tartaric acid, ascorbic acid, mandelic acid, 4-chloromandelic acid, lactic acid, glycolic acid, benzilic acid, vinylglucolic acid, citric acid, phenyllactic acid, tropic acid, atrolactic acid, dihydroxyfumaric acid, glycolic acid, quinic acid, hydroxymalonic acid, 2-hydroxysuccinic acid, tartronic acid, salicylic acid,
7. Esters of hydroxycarboxylic acids such as gluconic acid ethyl ester, tartaric acid diethyl ester, tartaric acid dimethyl ester, tartaric acid dibutyl ester, glycolic acid ethyl ester, xylitol dimethacrylate,
8. Dicarboxylic acids such as malonic acid, oxalic acid, fumaric acid, maleic acid, 2,3-dibromosuccinic acid, succinic acid, glutaric acid,
9. Phenolic compounds such as pyrocatechol, 4-tert.-butylpyrocatechol, 3,5-di-tert.-butylpyrocatechol, pyrogallol, salicylic alcohol, 3-methoxypyrocatechol, 2,3-dihydroxynaphthalene, 5-bromosalicylic alcohol, 5-chlorosalicylic alcohol, 4-chlorosalicylic alcohol, 3-chlorosalicylic alcohol, 3,5-dichlorosalicylic alcohol.

The use of several such OH-functional compounds is possible and can be expedient to establish special properties such as for example a desired chronological curing pattern.

The molar ratio between boric acid and the OH-functional compounds can be varied within a wide range from 1:0.1 to 1:10, the range from 1:1 to 1:4 being preferred.

The optimum ratio for each case depends on the necessary concentration in each case and the solubility of the complex, the equilibrium position and the effect of an excess of complexing agent on the properties of the dental materials.

Instead of boric acid, boric acid derivatives such as for example boric anhydride, borates and boric acid $C_{1-18}$, preferably $C_{2-4}$ esters can be wholly or partly used.

Furthermore the use of the starters according to the invention for the curing of the N-alkylaziridino compounds is also possible in combination with other known starter substances such as Brönsted acids or sulphonium salts, the described negative effects of the last-mentioned starters being reduced and their positive effects, such as for example good adjustability of the curing pattern being used.

There are various variants for the realization of the use according to the invention of the boric acid complexes as starter substances of polyether curing.

According to the first variant, the reaction is carried out before the formulation of the catalyst component, and the ester-like boric acid complex is used as a constituent of the catalyst component.

The preparation of the complex takes place in per se known manner, for example with the addition of toluene as entrainer for the water produced by esterification.

According to a second variant, the complexing of the boric acid is effected by mixing of boric acid or a boric acid derivative with the OH-functionalized compound(s) during the formulation of the catalyst component, the water produced by esterification either remaining in the catalyst component or being wholly or partly removed by suitable measures such as for example a vacuum treatment of the catalyst component.

Normally the formulation of the catalyst component takes place at temperatures in the range from 20 to 50° C., the application of higher temperatures can be expedient in accelerating the complexing or in establishing the desired water content.

When using the first and second variants, the base component can optionally also contain a neutral or basic-acting boric acid derivative such as for example alkali salts of boric acid or trialkyl esters of boric acid.

According to a third variant, the complex starting the curing is formed only after the mixing of the catalyst component with the base component, the catalyst component preferably containing the boric acid or a boric acid derivative and the base component the complexing agent.

According to a particular version of the third variant, the boric acid is present in the catalyst in a complexed or esterified form; after mixing with the base component, a recomplexing takes place.

According to a further version of the third variant, the complexing of the boric acid is effected by one or more compounds in which the OH groups of these compounds are derivatized. Upon mixing of the two components, the reactive boric acid complexes are formed.

A derivatization of the OH groups can be achieved for example by esterification, etherification or silylation, silylation being preferred.

The silylated complexing agents can be used both in the base component and in the catalyst component.

The listed variants and their versions can also be used in combination with each other. Such combinations can prove to be favourable in increasing the storage stability of the catalyst and base components.

To achieve specific mechanical properties or to achieve a desired setting pattern, it can be expedient to use combinations of boric acid complexes with varying structure and composition.

Usually, the catalyst components contain according to the preferred first and second variant:
(A) 0.1 to 100 wt.-% of at least one boric acid complex, optionally in an excess of complexing agent,
(B) 0 to 95 wt.-% of at least one inert diluent,
(C) 0 to 80 wt.-% of modifiers, including fillers, dyes, pigments, thixotropic agents, flow-improvers, polymeric thickeners, surfactants, stabilizers, polymerization-retarding compounds, odorous substances and flavourings,
the wt-% data being related in each case to the overall mass of the catalyst component;
and the base components:
(D) 5 to 100 wt.-% of a mixture of N-alkylaziridino compounds with aziridino equivalent masses of 500 to 25000 g/equivalent, preferably in the range from 1000 to 8000 g/equivalent and particularly preferably in the range from 2000 to 6000 g/equivalent,
(E) 0 to 95 wt.-% of at least one inert diluent,
(F) 0 to 80 wt.-% of modifiers, including fillers, dyes, pigments, thixotropic agents, flow-improvers, polymeric thickeners, surfactants, stabilizers, polymerization-retarding compounds, odorous substances and flavourings,
the wt-% data being related in each case to the overall mass of the base component;
and the components being stored separately and being mixed together for processing in a catalyst component to base component ratio of 5:1 to 1:20, preferably 1:1 to 1:10.

There can be used, as inert diluents according to constituents (B) and (E), polyether polyols, such as for example polypropylene glycols or mixed polyetherols with tetrahydrofuran and/or ethylene oxide and/or propylene oxide units, polyester polyols, such as for example polycaprolactone diols and polycaprolactone triols, polycarbonate diols, aliphatic esters, oils, fats, waxes, aliphatic hydrocarbons, araliphatic hydrocarbons and also mono- or multifunctional esters of multivalent acids such as for example phthalic acid, adipinic acid or citric acid or esters or amides of alkylsulphonic acids and arylsulphonic acids.

Constituent (B) or (E) is used in quantities of 0 to 95 wt.-%, preferably 10 to 90 wt.-% and particularly preferably 40 to 85 wt.-%, relative to the overall weight of the catalyst component or the base component.

As compounds according to the constituents (B) or (E), organic compounds can be used which hydrophobize the total mixture and belong to completely different compound classes.

Good results are achieved with hydrocarbons with 6 to 30 C atoms which are dissolved in the base component or can be incorporated in stable fine-particle form. The hydrocarbons can be aliphatic and/or aromatic and also olefinic and be present in branched and/or linear form.

Typical examples are polypropylene oils or polyisobutylene oils. Aromatic hydrocarbons such as for example polyphenylene compounds, dibenzyltoluene and dibenzylphenylmethane are used to advantage.

Waxy compounds with ester structures can also be used. Typical representatives of this compound class are the ester waxes such as are marketed for example by Hoechst under the name Hoechst-Wachs E; F; X 22.

Modifiers can be added to the catalyst component and also to the base component in a broad concentration range according to constituents (C) or (F). Constituents (C) or (F) are used in quantities of 0 to 80 wt.-%, preferably 0 to 50 wt.-% and particularly preferably in each case 15 to 40 wt.-%, relative to the overall weight of the catalyst component or base component.

These modifiers are mostly fine-particle fillers such as alumosilicates, silicic acids, quartz powder, wollastonite, mica powder and diatomaceous earth as well as dyes and pigments, the addition of which makes possible a better assessment of the mixed product and reduces the danger of confusion, thixotropic agents such as finely-dispersed silicic acids and other additives influencing the flow behaviour, such as polymeric thickeners, furthermore surfactants for establishing the flow-on behaviour and also odorous substances and flavourings.

As constituent (D) of the base component, mixtures of N-alkylaziridino compounds are used, the aziridino equivalent masses being able to be varied from 500 to 25000 g/equivalent and the number of N-alkylaziridino groups being able to be varied between 1 and 4 per molecule.

Preferably mixtures of N-alkylaziridino polyethers are used which consist of at least up to 60% of polyether compounds which carry at least two aziridino groups. According to another preferred version of the invention, mixtures of N-alkylaziridino polyethers are used which consist of at least up to 5% of polyether compounds which contain at least 3 aziridino groups.

Polyether basic bodies that can be used are those with tetrahydrofuran and/or ethylene oxide and/or propylene oxide units.

Preferably, the mixture of the N-alkylaziridino polyethers consists of mixed-polyether derivatives of ethylene oxide and tetrahydrofuran, incorporated in a molar ratio of 1:2 to 1:5, preferably 1:3 to 1:4.

Constituent (D) is used in concentrations of 5 to 100 wt.-%, preferably 20 to 70 wt.-% and particularly preferably 30 to 60 wt.-%, relative to the overall weight of the base component.

To establish the desired setting pattern, the preparations according to the invention according to constituent (C) or (F) can contain at least one curing-retarding compound. In principle, amine or alkaline substances retard the curing of the N-alkylaziridino compounds and can be used for this purpose.

Thus DE-A1-197 534 61, to the full contents of which reference is made here, describes the use of 0.0005 to 50 wt.-% of soluble and/or fine-particle alkaline-earth and/or alkali metal compounds.

Thus for example solutions of lithium compounds, such as lithium hydroxide or lithium carbonate, can be added to the catalyst component and/or the base component. The use of lithium carboxylates is also possible.

The two-component preparations according to the invention based on N-alkylaziridino compounds can be used, depending on the composition of the catalyst component and the base component, for the gluing of substrates, for sealing, coating and casting.

However, the preparations according to the invention are preferably used for the modelling of objects, models with accurate details being obtained with the preparations according to the invention due to their excellent flow-on behaviour.

The preparations according to the invention are used to particular advantage in dental modelling and in dental doubling.

In dental modelling, the good flow-on behaviour on the moist tooth and the moist gum as well as the insensitivity of the precision of the modelling vis-à-vis saliva and blood proves to be of great advantage.

In dental doubling, the good flow-on behaviour on hydrophilic plaster surfaces and the good wettability of the obtained doublings with plaster pulp or admixed investment compound formulations is advantageous.

The dosing of the two components can be carded out by sight, for example via the so-called strand-length comparison, by weight, via pre-dosed pack units and subsequent manual admixing, from double-chambered cartridges with static mixing tube or by means of volume dosing systems with downstream static or dynamic mixers.

A high mixing quality is required to achieve optimum results. On the other hand, the tolerance of the mixing ratio is in general relatively high and can for example cover the range from 0.75 to 1.25:5, with a preset catalyst component to base component ratio of 1:5, without use-restricting property changes being ascertained.

The invention is described in more detail by the following examples without being limited thereby.

EXAMPLES

1. Preparation and Testing of Impression Materials

With the help of laboratory kneaders, the catalyst components described in Table 1 were prepared on 100-g scale. The preparation of the base components which are described in Table 2 was carried out on 500-g scale.

Table 3 lists the mixtures which were examined using the catalyst components described in Table 1 and the base components described in Table 2, in the weight ratio indicated in each case. The mixtures were prepared by smoothing onto the mixing block within 30 seconds and used to determine the properties also listed in Table 3.

The mouth-removal time was able to be determined as the average value of each of 3 impressions from 3 different subjects in the form of a complete upper-jaw impression.

All mixtures of examples 1 to 10 according to the invention (Table 3) yielded impressions which were not sticky after removal from the mouth and were characterized by a very good design sharpness.

The individual components and also the mixtures did not display any unpleasant or noticeable odour.

2. Preparation and Testing of Doubling Materials

The catalyst components described in Table 4 were prepared on 100-g scale by mixing the organic components and incorporating the fillers with the help of a dissolver and homogenizing in a laboratory kneader.

The preparation of the base components described in Table 5 took place analogously on 100 g scale, the organic thixotropic additive used (Thixatrol ST) being dissolved at 55°–60° before the incorporation of the fillers.

The properties, obtained upon mixing of the components in the weight ratio 1:1, of the doubling materials are listed in Table 6.

The doubling materials according to invention examples 11 to 16 were characterized by an excellent design sharpness, a very good flow-on behaviour on hydrophilic plaster surfaces and an excellent wetting of the obtained doublings with plaster pulp or the admixed investment compound.

3. Preparation and Testing of Bite-Registration Materials

The catalyst components described in Table 7 and the base components described in Table 8 were prepared on 100-g or 500-g scale in laboratory kneaders.

Table 9 contains the characterization of the mixtures which were prepared by smoothing onto the mixing block within 25 seconds.

Furthermore, Table 9 contains the processing time of the mixtures obtained at 23° C., the mouth-removal time, each measured from the start of mixing and the shore A hardness after 24 hours.

The bite-registration materials according to invention examples 17 to 20 were characterized by a very high precision and were easy to cut and mill.

TABLE 1

Composition of the catalyst components for dental impression materials

| Constituent | AM-K1 | AM-K2 | AM-K3 | AM-K4 | AM-K5 | AM-K6 |
|---|---|---|---|---|---|---|
| Boric acid | 3.72 | 3.57 | 3.81 | — | 1.10 | 3.70 |
| Salicylic alcohol | 16.00 | 15.70 | 21.00 | — | 5.90 | — |
| Mandelic acid | — | — | — | — | — | 19.60 |
| Reaction product of boric acid with salicylic alcohol in the molar ratio 1:2 | — | — | — | 15.30 | 12.70 | — |
| Precipitation silicic acid (Sipernat D17) | 20.30 | 21.50 | 20.00 | 21.00 | 23.70 | 20.20 |
| Statistical mixed polyetherdiol, prepared from ethylene oxide and propylene oxide with a molar mass of 3200 g/mol | — | 58.53 | — | — | 25.30 | — |
| Polypropylene oxide diol with a molar mass of 2000 g/mol | — | — | 54.41 | 63.00 | 30.60 | 55.80 |
| Polypropylene oxide diol with a molar mass of 4000 g/mol | 59.28 | — | — | — | — | — |
| Lithium hydroxide | | | | 0.08 | | — |
| Coloring paste, red | 0.70 | 0.70 | 0.70 | 0.70 | 0.70 | 0.70 |

TABLE 2

Composition of the base components for dental impression materials

| Constituent | wt.-% | | |
|---|---|---|---|
| | AM-B1 | AM-B2 | AM-B3 |
| Mixture of bisaziridino polyethers with an average imino equivalent mass of 3100, prepared from a polyetherdiol which is composed of ethylene oxide and tetrahydrofuran units in the molar ratio 1:3.5 with a cyclic polyether content of 0.27% | 55.70 | 58.11 | 54.97 |
| Diatomaceous earth (Celatom MW 25) | 10.69 | 11.50 | 14.00 |
| Hydrogenated vegetable oil | 13.91 | 12.51 | 14.72 |
| Dibenzyl toluene | 17.80 | 9.08 | 9.41 |
| Statistical mixed polyetherdiol, prepared from ethylene oxide and propylene oxide with a molar mass of 3200 g/mol | — | 6.90 | — |
| Polypropylene oxide diol with a molar mass of 2000 g/mol | — | — | 5.00 |
| Coloring paste, grey | 1.90 | 1.90 | 1.90 |

TABLE 3

Elastomer materials according to the invention using the catalyst components according to Table 1 and base components according to Table 2 and determined properties

| | Invention examples-No. | | | | | | | | | |
|---|---|---|---|---|---|---|---|---|---|---|
| | 1 | 2 | 3 | 4 | 5 | 6 | 7 | 8 | 9 | 10 |
| Catalyst component | AM-K1 | AM-K1 | AM-K2 | AM-K2 | AM-K2 | AM-K3 | AM-K4 | AM-K5 | AM-K5 | AM-K6 |
| Base component | AM-B1 | AM-B2 | AM-B1 | AM-B2 | AM-B3 | AM-B1 | AM-B3 | AM-B1 | AM-82 | AM-B1 |
| Mixing ratio (by weight) C:B | 1:4.7 | 1:5.4 | 1:4.9 | 1:5.1 | 1:4.6 | 1:5.0 | 1:5.1 | 1:5.2 | 1:4.8 | 1:5.0 |
| Start of curing at 23° C. (seconds) | 120 | 120 | 130 | 125 | 135 | 150 | 125 | 145 | 140 | 40 |
| Mouth-removal time (seconds) | 260 | 245 | 280 | 270 | 290 | 275 | 280 | 250 | 240 | 120 |
| Elongation at break/% | 235 | 255 | 246 | 257 | 242 | 285 | 320 | 380 | 360 | 140 |
| Tensile strength/MPa | 1.65 | 1.75 | 1.89 | 1.85 | 1.95 | 1.84 | 1.90 | 2.01 | 2.10 | 1.35 |
| Shore A hardness after 24 h | 48 | 52 | 49 | 51 | 53 | 49 | 50 | 48 | 51 | 50 |

TABLE 4

Composition and viscosity of the catalyst components for doubling materials

| Constituent | wt.-% | | | | | |
|---|---|---|---|---|---|---|
| | DM-K1 | DM-K2 | DM-K3 | DM-K4 | DM-K5 | DM-K6 |
| Boric acid | 0.65 | 0.63 | 0.66 | — | 0.65 | 0.72 |
| 4-tert.-butylpyrocatechol | 3.49 | 3.42 | 3.55 | — | — | — |
| Pyrocatechol, silanized with dichlorodimethylsilane | — | — | — | — | 7.00 | — |
| Reaction product of boric acid with pyrocatechol in the molar ratio 1:1.95 | — | — | — | 2.40 | — | — |
| 1,6-hexanediol | 4.00 | 4.50 | — | — | 4.50 | — |
| L-(+)-tartaric acid diethylester | — | 6.00 | — | — | — | — |
| cis-1,4-butenediol | — | — | 5.86 | — | — | — |
| Glycolic acid | — | — | — | — | — | 0.8 |
| Glycerol | — | — | — | — | — | 1.65 |
| Alkyl sulphonic acid ester of phenol (Mesamoll) | 11.86 | 5.45 | 29.22 | 13.60 | 9.85 | 18.83 |
| Phthalic acid polyester (Ultramoll PP) | 66.00 | 66.00 | 47.00 | 70.00 | 66.00 | 66.00 |
| Precipitation silicic acid (Sipernat D10) | — | — | 4.90 | — | — | — |
| Precipitation silicic acid (Sipernat 22S) | 10.00 | 10.00 | 8.80 | — | — | 6.00 |
| Pyrogenic silicic acid (HDK H 2000) | 4.00 | 4.00 | — | 14.00 | 12.00 | 6.00 |
| Coloring pigment, yellow (Thermoplastgelb 084F) | — | — | 0.01 | — | — | — |
| Viscosity of the catalyst component/mPa.s | 3020 | 2480 | 1980 | 2250 | 2530 | 2620 |

TABLE 5

Composition and viscosities of the base components for doubling materials

| Constituent | wt.-% | | |
|---|---|---|---|
| | DM-B1 | DM-B2 | DM-B3 |
| Mixture of bisaziridino polyethers with an average imino equivalent mass of 3120, prepared from a polyetherdiol which is composed of ethylene oxide and tetrahydrofuran units in the molar ratio 1:3.4 | 40.00 | 39.70 | 45.00 |
| Diatomaceous earth (Celatom MW 25) | 16.00 | 15.30 | 10.00 |
| Dioctyl adipate (Plastomoll DOA) | 38.24 | 42.4998 | 40.50 |
| Block mixed polyether (Synperonic PE/L 121) | 5.00 | — | 2.50 |
| Modified castor oil derivative (Thixatrol ST) | 0.75 | 1.00 | — |
| Modified layered silicate (Bentone SD-3) | — | — | 2.00 |

TABLE 5-continued

Composition and viscosities of the base components for doubling materials

| | wt.-% | | |
|---|---|---|---|
| Constituent | DM-B1 | DM-B2 | DM-B3 |
| Coloring paste, white (Lithopone) | — | 1.50 | — |
| Dye, purple (Makrolex Violett B) | 0.01 | — | — |
| Dye, blue (Thermoplast Blau 684) | — | 0.0002 | — |
| Viscosity of the base component/mPa.s | 3460 | 3020 | 3950 |

TABLE 6

Tested mixtures and determined properties for doubling materials

| | Invention examples-No. | | | | | |
|---|---|---|---|---|---|---|
| | 11 | 12 | 13 | 14 | 15 | 16 |
| Catalyst component (cf. Table 4) | DM-K1 | DM-K2 | DM-K4 | DM-K3 | DM-K5 | DM-K6 |
| Base component (cf. Table 5) | DM-B1 | DM-B1 | DM-B1 | DM-B2 | DM-B1 | DM-B3 |
| Mixing ratio by weight | 1:1 | 1:1 | 1:1 | 1:1 | 1:1 | 1:1 |
| Start of curing/seconds | 195 | 675 | 135 | 315 | 240 | 215 |
| End of curing/seconds | 520 | 1800 | 420 | 855 | 780 | 760 |
| Shore A hardness after 24 hours | 23 | 19 | 18 | 22 | 16 | 25 |
| Tensile strength/N | 13.5 | 15.4 | 9.5 | 16.7 | 10 | 14.1 |
| Elongation at break/% | 131 | 192 | 127 | 201 | 160 | 170 |

TABLE 7

Composition of the catalyst components for bite-registration materials

| | Name of the catalyst components | | |
|---|---|---|---|
| Constituent | BM-K1 | BM-K2 | BM-K3 |
| Reaction product of boric acid and salicylic alcohol in the molar ratio 1:2.1 | — | 10.40 | 12.15 |
| Reaction product of boric acid and 5-bromosalicylic alcohol in the molar ratio 1:1.95 | 19.80 | 4.70 | 2.75 |
| Salicylic alcohol | — | — | 3.85 |
| Polypropylene oxide diol with a molar mass of 2100 g/mol | 53.75 | 57.85 | 55.80 |
| Precipitation silicic acid (Sipemat D17) | 25.70 | 26.30 | 24.70 |
| Coloring paste white | 0.75 | 0.75 | 0.75 |

TABLE 8

Composition of the base components for bite-registration materials

| | Name of the base component wt.-% | |
|---|---|---|
| Constituent | BM-B1 | BM-B2 |
| Mixture of bisaziridino polyethers with an average imino equivalent mass of 3100, prepared from a polyetherdiol which is composed of ethylene oxide units and tetrahydrofuran units in the molar ratio 1:3.6 and has a cyclic ether content of 0.31 | 58.10 | 25.00 |
| Mixture of bisaziridino polyethers with an average imino equivalent mass of 1600, prepared from a polyetherdiol which is composed of ethylene oxide units and tetrahydrofuran units in the molar ratio 1:3.4 and has a cyclic ether content of 0.38 | — | 29.75 |
| Diatomaceous earth (Celatom MW 25) | 34.00 | 39.27 |
| Hydrogenated vegetable oil | 5.00 | 4.20 |
| Dibenzyl toluene | 2.90 | 1.68 |

TABLE 9

Bite-registration materials according to the invention using the catalyst components according to Table 7 and the base components according to Table 8 and determined properties

| | Invention examples-No. | | | |
|---|---|---|---|---|
| | 17 | 18 | 19 | 20 |
| Catalyst component (cf. Table 7) | BM-K1 | BM-K2 | BM-K2 | BM-K3 |
| Base component (cf. Table 8) | BM-B1 | BM-B1 | BM-B2 | BM-B2 |
| Mixing ratio (by weight) C:B | 1:5.0 | 1:5.3 | 1:4.8 | 1:5.0 |
| Processing time/seconds | 50 | 45 | 70 | 80 |
| Mouth-removal time/seconds | 140 | 120 | 160 | 150 |
| Shore A hardness (after 24 h) | 71 | 73 | 81 | 83 |

What is claimed is:

1. Elastomer material based on N-alkylaziridino compounds with a base component which contains an aziridino compound and with a catalyst component which contains at least one acid-acting compound, both components being mixed before use, wherein, as the acid-acting compound of the catalyst component, one or more boric acid complexes are used which can be obtained by reaction of boric acid and/or a boric acid derivative with at least one OH-functional compound, the OH functions being able to be present wholly or partly protected, and this reaction being carried out either as an upstream reaction between boric acid and/or a boric acid derivative and at least one such OH-functional compound or during or after the preparation of the catalyst component or by mixing the catalyst component with the base component which then contains at least one such OH-functional compound and the at least one OH-functional compound containing at least one and up to 10 OH groups wherein the OH-functional compound is selected from the group consisting of
   i) compounds which contain at least one 1,2-dihydroxy and/or at least 1,3-dihydroxy group;
   ii) compounds which have at least one phenolic OH group; and
   iii) α-hydroxy-carboxylic acids,
wherein the OH-functional compound containing at least one and up to 10 OH groups has the general structural formula

wherein R1, R2 and R3 represent the same or different radicals selected from the group consisting of hydrogen, aliphatic, cycloaliphatic, aromatic and araliphatic substituents with 1 to 30 C atoms in each, of which one or more C atoms can be replaced by

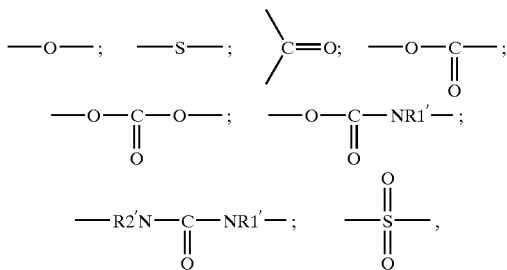

R1' and R2' being the same or different wherein R1' and R2' are aliphatic, cycloaliphatic, aromatic or araliphatic bivalent radicals with 1 to 30 C atoms.

2. Elastomer material according to claim 1, wherein the curing of the aziridino compounds takes place through boric acid complexes which correspond to the following general structural formula,

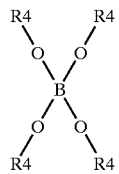

in which the substituents R4 can be different or the same or bridged with each other and R4 can mean: hydrogen, an aliphatic, cycloaliphatic, aromatic or araliphatic radical with 1 to 30 C atoms and one or more C atoms can be replaced by

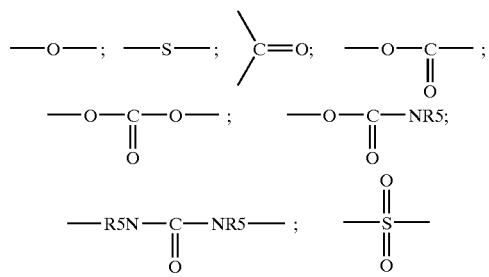

in which R5 is hydrogen or C1 to C12 alkyl and R4 and also R5 can carry one or more halogens, —CN, —OH, —SH, —COOH, —COO($C_{1-18}$ alkyl), —$NO_2$, $SO_3H$, alkylthio-, keto- and also aldehyde groups as substituents.

3. Elastomer material according to one of claims 1 to 2, wherein the catalyst component contains 0.1 to 100 wt.-% of boric acid complexes with OH-functional compounds optionally in an excess of these OH-functional compounds.

4. Elastomer material according to claim 1, wherein the ratio of number of mols of boron in the catalyst component to the number of aziridino equivalents in the mixed preparation is 1:1 to 1:20.

5. Elastomer material according to claim 1, wherein the boric acid complexes are prepared by reaction of boric acid or boric acid derivatives with compounds which contain at least two OH groups or in that the boric acid complexes are prepared by reaction of boric acid esters with compounds which contain at least two OH groups.

6. Elastomer material according to claim 1, wherein the reaction of the boric acid or the boric acid derivative with the OH-functional compounds is carried out before the formulation of the catalyst component and the ester-like boric acid complex is used as a constituent of the catalyst component, or in that the reaction of the boric acid or the boric acid derivative with the OH-functional compounds takes place during the formulation of the catalyst component, or in that the reaction of the boric acid or the boric acid derivative with the OH-functional compounds takes place during and after the mixing of the catalyst component with the base component.

7. Elastomer material according to claim 1, wherein the formation of the curing-triggering boric acid complex takes place during and/or after the mixing of the catalyst component with the base component from a boric acid derivative of the catalyst component and at least one OH-functional compound with at least 2 OH groups of the base component.

8. Elastomer material according to claim 1, wherein the formation of the curing-triggering boric acid complex takes place during and/or after the mixing of the catalyst component with the base component at least partly from a boric acid derivative, preferably a boric acid ester, of the catalyst component and at least one OH-functional compound of the base component.

9. Elastomer material according to claim 1, wherein a molar ratio between boric acid and the OH-functional compounds is from 1:0.1 to 1:10.

10. Elastomer material according to claim 1, wherein, as complexing agent for the boric acid, OH-functional organic compounds are used which contain at least one 1,2-dihydroxy and/or at least one 1,3-dihydroxy group.

11. Elastomer material according to claim 1, wherein OH-functional complexing agents are used which have at least one phenolic OH group.

12. Elastomer material according to claim 11, wherein, as complexing agent, pyrocatechol or 2,3-dihydroxynaphthalene is used, the phenyl radical(s) optionally being able to contain further substituents such as alkyl, halide, alkyl ester, alkyl ether, carboxyl and/or hydroxyl, or in that salicylic alcohol is used as complexing agent, the phenyl radical optionally being able to contain further substituents such as alkyl, halide, alkyl ester, alkyl ether, carboxyl and hydroxyl.

13. Elastomer material according to claim 1, wherein, as complexing agent, α-hydroxycarboxylic acids are used.

14. Elastomer material according to claim 1, wherein, as complexing agents, compounds with protected OH groups are used.

15. Elastomer material according to claim 1, wherein several complexing agents are used.

16. Elastomer material according to claim 1, wherein combinations of boric acid complexes with varying structure and composition are used.

17. Elastomer material according to claim 16, wherein, as complexing agent, 4-tert.-butylpyrocatechol is used in combination with an aliphatic OH-functional compound.

18. Elastomer material according to claim 1, wherein the boric acid complexes are used together with other starters.

19. Process for the preparation of elastomer materials based on N-alkylaziridino compounds with a base component which contains an aziridino compound and with a catalyst component which contains at least one acid-acting compound, both components being mixed before use, wherein, as the acid-acting compound of the catalyst component, one or more boric acid complexes are used which can be obtained by reaction of boric acid and/or a boric acid derivative with at least one OH-functional compound, the OH functions being able to be present wholly or partly protected, and this reaction being carried out either as an upstream reaction between boric acid and/or a boric acid derivative and at least one such OH-functional compound or during or after the preparation of the catalyst component or by mixing the catalyst component with the base component which then contains at least one such OH-functional compound and the at least one OH-functional compound containing at least one and up to 10 OH groups has the general structural formula

wherein R1, R2 and R3 represent the same or different radicals selected from she group consisting of hydrogen, aliphatic, cycloaliphatic, aromatic and araliphatic substituents with 1 to 30 C atoms in each, of which one or more C atoms can be replaced by

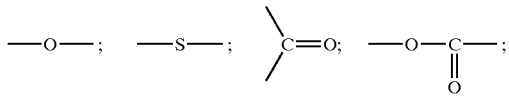

-continued

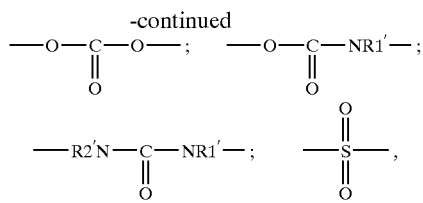

R1' an R2' being the same or different wherein R1' and R2' are aliphatic, cycloaliphatic, aromatic or araliphatic bivalent radicals with 1 to 30 C atoms.

20. A dental molding comprising the elastomer materials according to claim 1.

21. Kit which contains the base component and the catalyst component according to claim 1 separately from each other.

22. The dental molding according to claim 20, wherein the dental molding is a bite-registration material or a doubling material.

23. The elastomer material according to claim 9, wherein the molar ratio between boric acid and the OH-functional compounds is 1:1 to 1:4.

24. The elastomer material according to claim 9, wherein the molar ratio between boric acid and the OH-functional compounds is 1:1.5 to 1:3.

25. The elastomer material according to claim 13, wherein the α-hydroxycarboxylic acids are selected from the group consisting of glycolic acid, mandelic acid and benzilic acid.

26. The elastomer material according to claim 14, wherein the compounds with protected OH groups are silylated.

27. The elastomer material according to claim 18, wherein the other starters are sulphonium starters.

* * * * *

UNITED STATES PATENT AND TRADEMARK OFFICE
CERTIFICATE OF CORRECTION

PATENT NO. : 6,894,144 B1
APPLICATION NO. : 10/070376
DATED : May 17, 2005
INVENTOR(S) : Joachim W. Zech It is certified that error appears in the above-identified patent and that said Letters Patent is hereby corrected as shown below:

Column 2
Line 25, delete "materials" and insert -- material --, therefor.

Column 7
Line 39, delete "carded" and insert -- carried --, therefor.

Columns 9-10
Line 2, in (Col. 9), in (Table 3), under (Invention examples-No.), delete "AM-82" and insert -- AM-B2 --, therefor.

Column 11
Line 55, in (Table 7), below "Name of the catalyst components" insert -- wt.-% --.

Line 64, in (Col. 1), in (Table 7), delete "(Sipemat" and insert -- (Sipernat --, therefor.

Line 65, in (Col. 1), in (Table 7), delete "paste" and insert -- paste, --, therefor.

Column 13
Line 50, in Claim 2, delete "NR5;" and insert -- NR5–; --, therefor.

Column 15
Line 28, in Claim 19, delete "she" and insert -- the --, therefor.

Signed and Sealed this

Thirteenth Day of May, 2008

JON W. DUDAS
*Director of the United States Patent and Trademark Office*